(12) United States Patent
Kikuchi et al.

(10) Patent No.: US 7,951,344 B2
(45) Date of Patent: May 31, 2011

(54) LIQUID ANALYSIS SYSTEM AND CARTRIDGE

(75) Inventors: Yoshihiko Kikuchi, Kawasaki (JP); Kazuo Kusakabe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 912 days.

(21) Appl. No.: 11/267,127

(22) Filed: Nov. 7, 2005

(65) Prior Publication Data

US 2006/0099111 A1    May 11, 2006

(30) Foreign Application Priority Data

Nov. 9, 2004  (JP) ................................. 2004-325393
Sep. 13, 2005  (JP) ................................. 2005-266022

(51) Int. Cl.
G01N 21/00 (2006.01)
B01L 3/00 (2006.01)
A61J 1/06 (2006.01)

(52) U.S. Cl. ..................... 422/554; 422/503; 422/82.05; 422/82.11; 422/68.1; 422/50; 436/180

(58) Field of Classification Search .............. 422/82.11, 422/68.1, 82.05, 50, 100
See application file for complete search history.

(56) References Cited

U.S. PATENT DOCUMENTS

| | | | |
|---|---|---|---|
| 5,370,842 A | 12/1994 | Miyazaki et al. | 422/82.06 |
| 6,082,185 A | 7/2000 | Saaski | 73/64.56 |
| 6,136,611 A | 10/2000 | Saaski et al. | 436/527 |
| 2002/0119077 A1* | 8/2002 | Shumate et al. | 422/100 |
| 2004/0137607 A1 | 7/2004 | Tanaami et al. | |
| 2005/0148091 A1 | 7/2005 | Kitaguchi et al. | 436/164 |
| 2006/0165558 A1* | 7/2006 | Witty et al. | 422/58 |

FOREIGN PATENT DOCUMENTS

| | | |
|---|---|---|
| EP | 1878802 A1 * | 1/2008 |
| JP | 7-119688 | 12/1995 |
| JP | 10-62433 | 3/1998 |
| JP | 2832117 | 9/1998 |
| JP | 2004-77305 | 3/2004 |
| JP | 2004-212361 A | 7/2004 |
| WO | WO 01/13127 A1 | 2/2001 |

* cited by examiner

*Primary Examiner* — Jill Warden
*Assistant Examiner* — Dean Kwak
(74) *Attorney, Agent, or Firm* — Fitzpatrick, Cella, Harper & Scinto

(57) ABSTRACT

An apparatus main body is loaded with a cartridge that contains a sensor and is capable of processing liquid contained in it without moving it from the inside to the outside of the cartridge. The cartridge is loaded into the apparatus main body in such a way that the direction of feeding liquid in the span of the flow channel where the sensor is arranged is vertical and the cartridge can be accessed from the apparatus main body from above.

27 Claims, 6 Drawing Sheets

LIQUID ANALYSIS SYSTEM AND CARTRIDGE

BACKGROUND OF THE INVENTION

1. Field of the Invention

This invention relates to an analysis system for detecting a specific object in liquid and a cartridge for containing the object of analysis and a reagent to be used for such an analysis system.

2. Related Background Art

Detecting a particular object contained in a specimen by means of an optical technique or an electric technique is a practice that is popular in various fields of technology and industry. Optical techniques that can be used for such a detection practice include detection of absorbed light, that of fluorescent light and that of emitted light. Electric techniques, on the other hand, include the use of amperometry, that of voltammetry and an electrode method similar to the preceding methods as well as the use of field effect transistors, quartz oscillators or some other electronic parts to detect a particular object.

Apparatus for qualitatively or quantitatively measure a particular object include those that are adapted to bring a specimen into contact with a sensor and those adapted to automatically carry out a plurality of necessary steps including a reaction step, a cleansing step and a preprocessing step.

U.S. Pat. Nos. 6,136,611 and 6,082,185 propose a cartridge that contains optical fibers having a particular profile and adapted to operate as sensor, a liquid feed flow channel being dug therein. The use of a cartridge as part of a measurement apparatus is important to make a site of the apparatus that can be contaminated by the specimen disposable. Additionally, such a cartridge is important as means for supplying a reagent by an amount necessary for measurement. Cartridges comprising tanks for storing a specimen and a plurality of different reagents are also being popularly used. Japanese Patent No. 2077364 and Japanese Patent Application Laid-Open No. H10-062433 disclose the use of such a cartridge so that the liquid contained in each of the tanks is conveyed by a mechanism arranged at the side of the main body of the apparatus.

In recent years, many plate-shaped molded products that appear like single slide glass plate and integrally comprise liquid feed flow channels, containing tanks and reaction tanks have become popular. The pamphlet of International Publication No. WO01/013127 discloses a cartridge comprising a plate on the surface of which a plurality of reservoirs and capillaries are dug in and connected to a compressed air feed system by way of a diaphragm. Japanese Patent Application Laid-Open No. 2004-77305 discloses a microchip comprising a substrate in which a flow channel is formed and a part of the flow channel operates as optical waveguide and is connected to an external coaxial optical fiber so that light may be injected into and received by the optical waveguide. Cartridges containing a liquid feed mechanism in the inside are also known. For example, Japanese Patent No. 2832117 discloses a cartridge comprising a liquid flow channel in which a heat emitting element is arranged to boil and bubble liquid and the boiling and bubbling liquid is used to provide power for driving and feeding liquid.

SUMMARY OF THE INVENTION

When arranging a sensor element in a flow channel, the flow channel shows a long span relative to the diameter thereof if a large measurement surface area has to be secured without excessively enlarging the diameter of the flow channel. Such a span defines the longitudinal direction of the entire cartridge when it is wanted to make the cartridge compact or for the convenience of the manufacturing process. More specifically, when the cartridge is a rectangular parallelepiped, the cartridge is so designed that flow channel runs in parallel with the widest lateral surface in that span. When a measurement apparatus is adapted to handle a plurality of such cartridges, it is desired that the cartridges may be loaded in a highly compact state and the cartridges may be individually accessible from the apparatus side. Additionally, it is desired that each of the cartridges may be accessed with a reliable degree of positional accuracy and the apparatus main body is practically free from contamination attributable to the cartridges.

Thus, the object of the present invention is to provide a liquid analysis system that meets the above, listed requirements and is compact and operable with a high degree of accuracy.

In an aspect of the present invention, the above object is achieved by providing a liquid analysis system designed to operate a cartridges loaded in the apparatus main body;

the cartridge having a flow channel system capable of carrying out a complete process on liquid within the cartridge, a sensor arranged in part of the flow channel system and a ceiling surface provided with a signal output section for outputting signals from the sensor to the apparatus main body;

the part of the flow channel carrying the sensor extending in a direction allowing fluid to be fed in a vertical direction at the time of loading the cartridge in an apparatus main body; and the apparatus main body having a reception section adapted to be arranged opposite to the signal output section arranged on the ceiling surface and receive the signals from the signal output section.

In another aspect of the present invention, there is provided a cartridge for liquid analysis adapted to be loaded in an apparatus main body, the cartridge comprising:

a flow channel system capable of carrying out a complete process on liquid within the cartridge, a sensor arranged in part of the flow channel system and a ceiling surface provided with a signal output section for outputting the signals from the sensor to the apparatus main body;

the part of the flow channel carrying the sensor extending in a direction allowing fluid to be fed in a vertical direction at the time of loading the cartridge in the apparatus main body.

In still another aspect of the present invention, there is provided a liquid analysis system designed to operate a cartridge loaded in an apparatus main body;

the cartridge having a flow channel system capable of carrying out a complete process on liquid within the cartridge, a sensor arranged in part of the flow channel system, a signal output section for outputting signals from the sensor to the apparatus main body and a drive force input section for receiving the drive force from the apparatus main body side for controlling the flow of liquid;

the signal output section and the drive force input section being arranged at a same lateral surface of the cartridge;

the apparatus main body having a reception section adapted to be arranged opposite to the signal output section arranged on the lateral surface and receive the signals from the signal output section and a drive force transmission means adapted to be arranged opposite to the drive force input section arranged on the lateral surface and apply drive force to the drive force input section.

In a further aspect of the present invention, there is provided a cartridge for liquid analysis adapted to be loaded in an apparatus main body, the cartridge comprising:

a flow channel system capable of carrying out a sensor arranged in part of the flow channel system, a signal output section for outputting the signals from the sensor to the apparatus main body and a drive force input section for receiving the drive force for controlling the flow of liquid from the transmission means at the apparatus main body side;

the signal output section and the drive force input section being arranged at a same lateral surface of the cartridge.

Thus, the present invention can provide a compact analysis/measurement system that shows a high operation accuracy level. The system can prevent the measurement apparatus main body from being contaminated by reagents and the specimen to be examined and improve the level of accuracy of measurement and that of maintenance of the apparatus.

Other features and advantages of the present invention will be apparent from the following description taken in conjunction with the accompanying drawings, in which like reference characters designates the same or similar parts throughout the figures thereof.

BRIEF DESCRIPTION OF THE DRAWINGS

FIG. 5A is a schematic vertical cross sectional view, FIG. 5B is a schematic horizontal cross sectional view taken at or near the ceiling surface and FIG. 5C is a schematic horizontal cross section view taken at or near the bottom surface;

DESCRIPTION OF THE PREFERRED EMBODIMENTS

Preferred embodiments of the present invention will now be described in detail in accordance with the accompanying drawings.

A most suitable system realized by applying the present invention comprises an optical waveguide arranged along a flow channel so as to operate as sensor and light is input to and output from the apparatus main body of the system above the optical waveguide.

Figure 1:
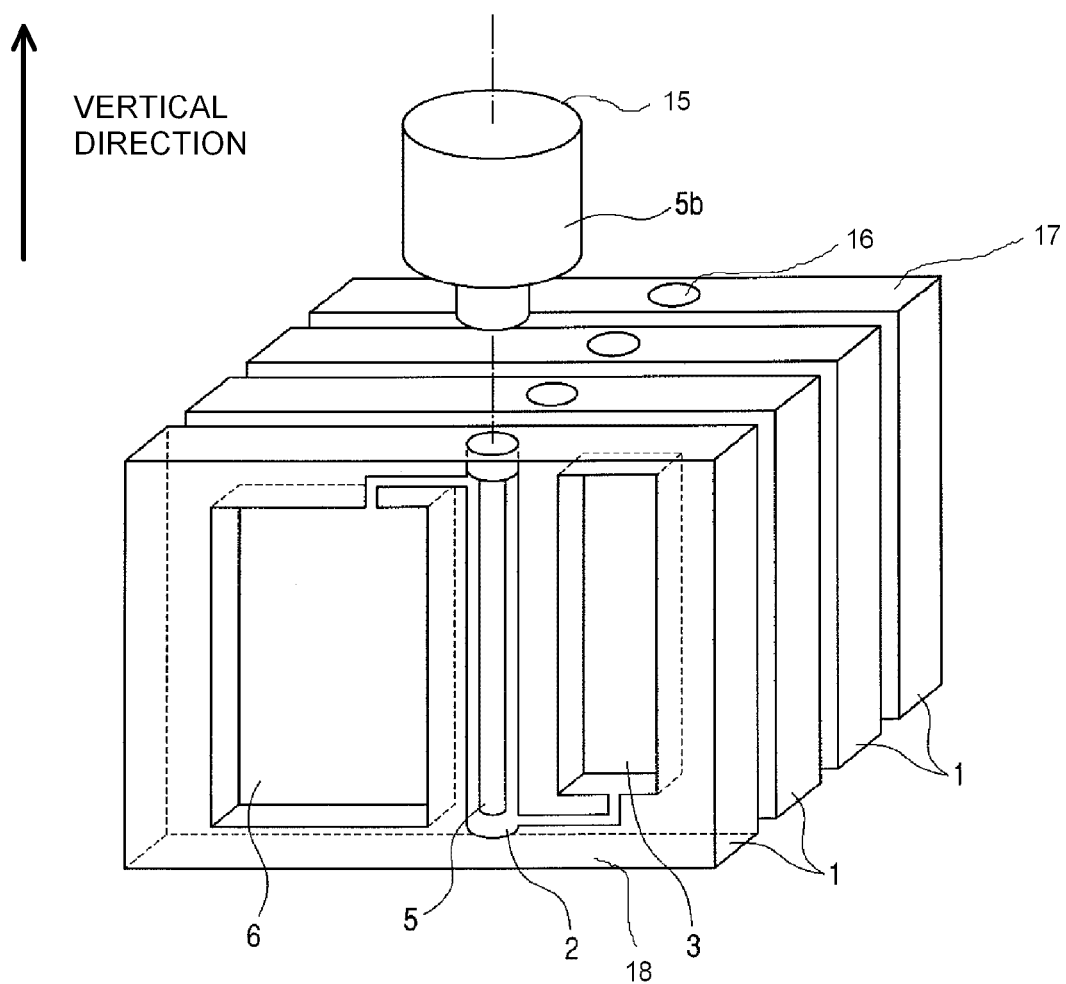
FIG. 1 is a schematic illustration of an analysis system according to the invention showing how cartridges are loaded.

FIG. 1 shows how cartridges are loaded in the apparatus. The direction in which some of the principal parts thereof are arranged is in focus. For the purpose of simplicity, some other parts are omitted. Note that the detailed arrangement of the cartridges is not limited to the illustrated one.

FIG. 1 shows four rectangular parallelepiped cartridges that are arranged in parallel with each other in a transversal direction. Note that the flow channel system in each of the cartridges 1 is the simplest one formed by arranging a single specimen liquid tank 3 and a single waste liquid tank 6. The liquid to be examined is injected into the specimen liquid tank 3 and fed through the flow channel 2. When the specimen liquid is supplied to optical waveguide 5, which operates as a sensor and is arranged midway in the flow channel 2, it is subjected to measurement by the optical waveguide 5. The liquid is then moved from the optical waveguide 5 to and collected by the waste liquid tank 6. In the rectangular parallelepiped cartridges 1, the flow channel system that includes tanks 3 and 6, particularly the long span of the flow channel where the optical waveguide 5 is disposed, is arranged so as to run in parallel with the largest surfaces of the rectangular parallelepiped. Reference number 15 represents a reception section, reference number 16 represents a signal output section, reference number 17 represents a ceiling surface, and reference number 18 represents a bottom surface. This arrangement allows the flow channel system to be formed with ease. Then, the obtained cartridge will be highly compact.

The plurality of cartridges are arranged in parallel with each other in a transversal direction in such a way that their surfaces having the largest area are placed opposite to each other. With this arrangement, each cartridge can contain an analyzing instrument most compactly. The cartridges are arranged in such a way that the long span of the flow channel where the optical waveguide 5 is disposed in each cartridge extends in a vertical direction. More specifically, the span of the flow channel extends vertically or substantially vertically as linear flow channel so that it is possible to provide a sufficient contact area and a sufficient contact time between the optical waveguide and the liquid, while effectively feeding liquid to the optical waveguide.

On the other hand, the end facets of the optical waveguide 5 that can operate as input/output terminals are directed upward and connected to the optical system 5b and the optical waveguide 5 for actually detecting light at the apparatus main body side in a contact or non-contact manner.

The structure of each cartridge illustrated in FIG. 1 and the method of containing a plurality of cartridges provides the following three advantages.

Firstly, it is possible to access the sensors of the cartridges individually from the apparatus main body in a state where the cartridges are arranged side by side as shown in FIG. 1. This is particularly advantageous from the viewpoint of downsizing the cartridge storage area and the access a mechanism and its periphery.

Secondly, the risk of contaminating the optical system by dirt and/or leaking liquid, if any, is low because the optical waveguide of the sensor and the optical system of the detecting means at the apparatus side can be brought into contact in a vertical direction on the top surface of the cartridge. It will be appreciated that the risk of contaminating the optical system by dirt and/or leaking is high when the cartridges are laid flat or arranged upside down. Additionally, when the lens barrel of the optical system is moved relative to the cartridges for mutual engagement, they can be aligned more accurately when the lens barrel is accessed from above because then the direction of the gravity a applied to the lens barrel and the moving direction of the barrel agree with each other.

Thirdly, it is possible to raise the efficiency of feeding liquid when liquid is fed in a vertical direction in a major part of the flow channel. More specifically liquid moves vertically downwardly in the specimen tank 3 whereas it moves vertically upwardly at a part of the flow channel where the sensor is arranged. Then, pressure can be applied with ease due to the weight of the liquid itself in the tank so that liquid flows smoothly from the outlet port of the tank. If the tank is oblong in a vertical direction, it is possible to finely control the flow rate, utilizing the length of the tank. Additionally, as the flow channel is filled with liquid from below in the part thereof where the sensor is arranged, the air in the flow channel can be smoothly forced out.

Furthermore, when the flow channel has a part whose diameter is greater than a capillary, the air bubbles that are formed for some reason or another can easily be drawn out into the space located above it.

The above-described advantages are also available when the optical sensor is replaced by an electric sensor.

Now, the mechanism for controlling the flow of liquid in a cartridge will be described below. In an analysis system according to the present invention, drive force is applied to the cartridge from the apparatus main body side in order to control the flow of liquid in the cartridge. The flow of liquid in the cartridge is preferably controlled in such a way that a structure for raising or reducing the pressure being applied to the cartridge by utilizing the drive force transmitted to the cartridge from the apparatus main body side is arranged along the flow channel system. In other words, with such a structure, liquid is moved (fed) due to the pressure or the pressure reduction applied to the liquid in the flow channel system by the drive force transmitted from the apparatus main body. Three preferable modes of realizing such a drive force transmitting means for the purpose of the present invention include the following.

(1) The use of a blast pipe that transmits the pressure change to the liquid in the cartridge by way of a gas layer from the pump arranged in the apparatus main body.

(2) The use of a link rod that transmits the mechanical force of the motor arranged in the apparatus main body to the liquid in the cartridge by way of a piston mechanism.

(3) The use of a pinch roller that transmits the mechanical force of the motor arranged in the apparatus main body to the liquid in the cartridge by way of a flexible and elastic diaphragm.

Preferable detailed configurations of the cartridge and its periphery that can be use for the purpose of the present invention include the following.

(A) The flow channel system has a plurality of tanks for storing liquid and cartridges are loaded in the apparatus main body in such a way that the longitudinal directions of the tanks are substantially vertical.

(B) The structure for connecting the blast pipe is so configured that a needle pipe arranged at an end of the blast pipe can be plugged into and pulled out from the aperture arranged in the cartridge and closed by a flexible and elastic diaphragm.

(C) The transmission means is connected at a plurality of positions that are arranged close to each other.

Preferably, the apparatus main body is so configured that it comprises a magazine rack for removably loading a plurality of cartridges and a mechanism for horizontally translating the magazine rack in the direction along which the cartridge are arranged. Preferably, the magazine rack has a mechanism for automatically and collectively discharging the cartridges after use.

The flow channels and the tanks of the flow channel system may show a circular, elliptic, rectangular or some other appropriate cross section when taken in a direction perpendicular to the flow channels depending on the structure of the cartridges and the process for manufacturing them.

As shown in FIG. 1, the liquid to be analyzed that is contained in a cartridge according to the invention is analyzed and disposed without being taken out from the cartridge. In short, a cartridge according to the invention comprises a flow channel system that is capable of carrying out a complete analytic process on the liquid to be analyzed only within the cartridge.

Now, an example of the internal structure of the cartridge and a technique of driving and feeding liquid will be described by referring to FIGS. 2 through 4. These drawings illustrate relatively simple embodiments in terms of the number of tanks and the mode of linking the tanks and the structure of the cartridges and that of the drive force transmission system are not limited to those illustrated in the drawings.

Figure 2:
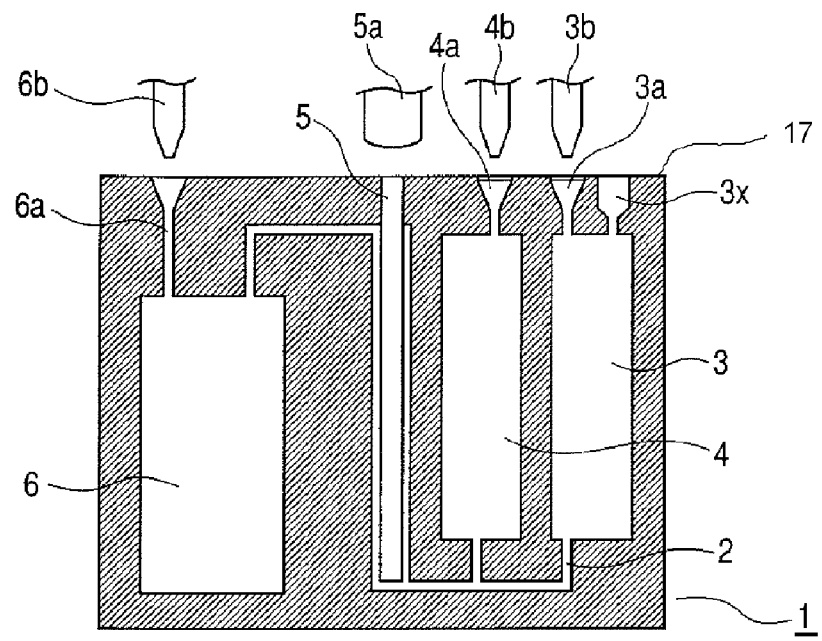
FIG. 2 is a schematic cross sectional view of an embodiment of cartridge and a peripheral mechanism thereof, showing the configuration thereof.
Figure 3:
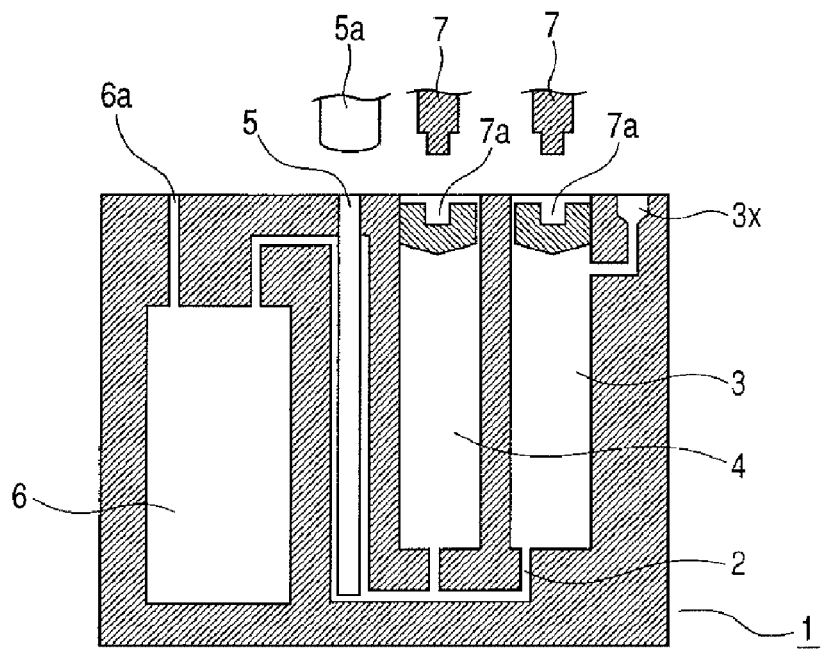
FIG. 3 is a schematic cross sectional view of another embodiment of cartridge and a peripheral mechanism thereof, showing the configuration thereof.
Figure 4:
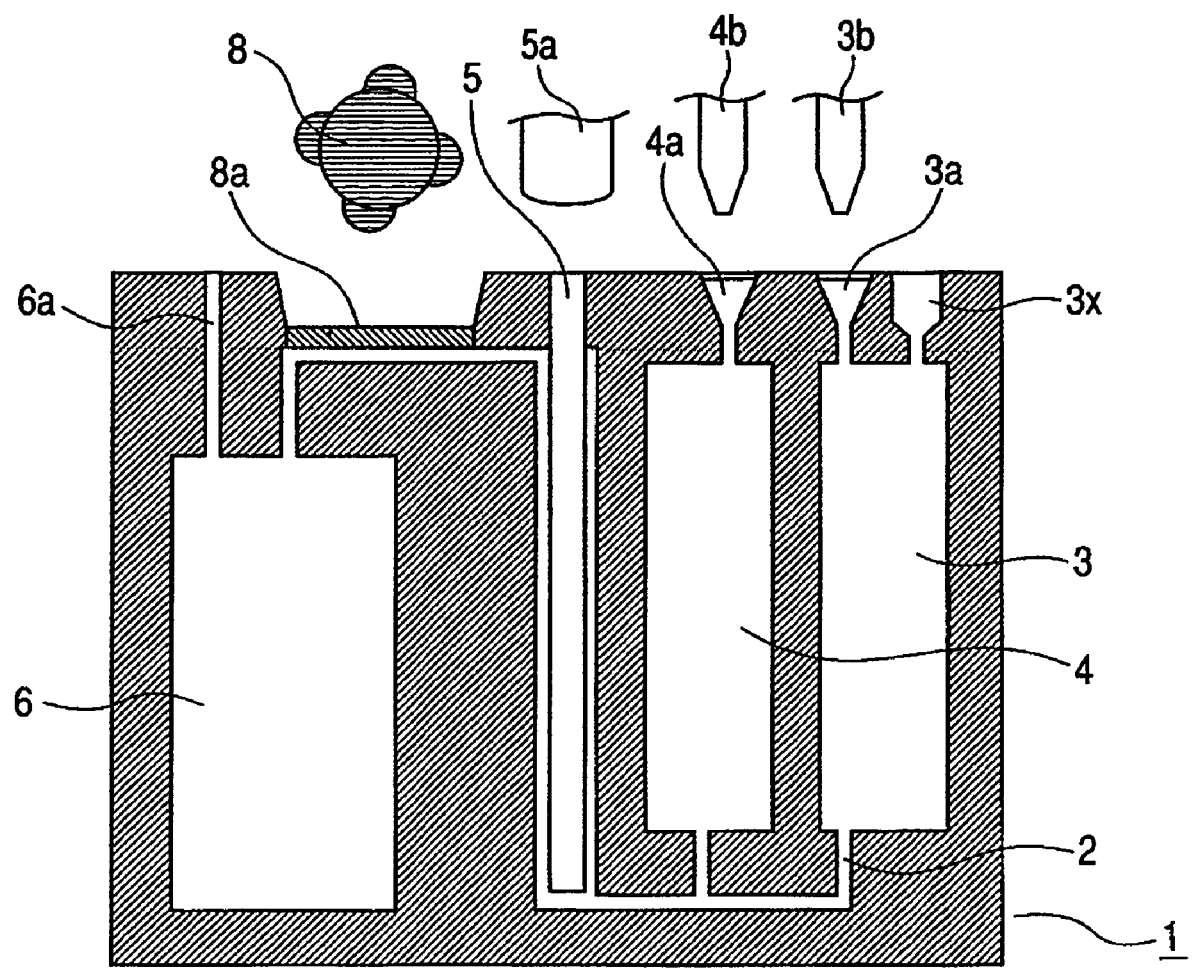
FIG. 4 is a schematic cross sectional view of still another embodiment of cartridge and a peripheral mechanism thereof, showing the configuration thereof.

All the embodiments of cartridge according to the invention and illustrated in FIGS. 2 through 4 have three tanks including a specimen tank 3. The liquid to be examined is injected into the specimen tank 3 from outside before the cartridge is loaded and contained in the apparatus main body (not shown). The specimen tank 3 has an injection port $3x$ provided with a mechanism for closing the injection port $3x$ after injecting the liquid. The mechanism may include a sealing door that can be automatically or manually closed. The lateral wall of the injection port $3x$ may be formed by using a flexible material. Then, the injection port $3x$ may be closed by crushing it by hand or by means of a tool after injecting the liquid into the specimen tank 3. Alternatively, the lateral wall of the injection port $3x$ may be formed by using an elastic material. Then, the liquid may be injected by way of an injection pipe and the injection pipe may be pulled out to automatically close the injection port $3x$ after injecting the liquid into the specimen tank 3. Still alternatively, the injection port $3x$ may be provided with a permanent lid made of an elastic material and a syringe needle may be used to inject the liquid through the lid. Then, the liquid inside the specimen tank 3 would not leak out when the pin hole formed through the lid is closed by some sealing mechanism.

The three tanks also include a reagent tank 4 for containing liquid in advance that by turn contains a reagent that participates in a reaction relating to the measurement to be conducted and a waste liquid tank 6 for containing the specimen and the reagent after the measurement operation so that the waste liquid may not be transferred to the outside of the cartridge. The liquid in the specimen tank 3 and the liquid in the reagent tank 4 are forced out from the respective tanks by way of a flow channel 2 and brought into contact with the optical waveguide 5 before they are transferred into the waste liquid tank 6.

The tanks of each of the illustrated embodiments of cartridge have a profile linearly extending from the bottom surface 18 of the cartridge to the ceiling surface 17. In other words, the tanks have a profile whose length is greater than its width. The cartridge is loaded in the apparatus main body in such a way that the longitudinal directions of the tanks come to agree with the vertical direction in the apparatus main body. As a result of using tanks that have such a structure, the tanks can be arranged efficiently in the flow channel system and allow the cartridge to be downsized with ease.

With the cartridge illustrated in FIG. 2, liquid is moved from a tank to another by applying air pressure to the liquid. When the cartridge 1 is loaded into the apparatus main body (not shown), blast pipes $3b$, $4b$, $6b$ are linked respectively to air flow channels $3a$, $4a$, $6a$ that communicate with the respective tanks 3, 4, 6 from the apparatus main body. The blast pipes are provided with respective valves so that the flow rate of the liquid from each of the tanks can be controlled by opening or closing the corresponding valve and raising or reducing the air pressure being applied to the liquid from an air pump. For example, only the liquid in the specimen tank 3 can be driven to move toward the waste liquid tank 6 by opening the blast pipes $3b$ and $6b$ and closing the blast pipe 4b, while raising pressure from the blast pipe 3b. The same effect can be achieved alternatively by reducing pressure from the blast pipe 6b instead of raising pressure from the blast pipe 3b. Still alternatively, the same effect can be achieved by raising pressure from the blast pipe 3b and reducing pressure from the blast pipe 6b at the same time. The rate at which liquid is fed can be controlled by way of the rate at which air is injected or drawn.

FIG. 3 illustrates another embodiment of cartridge according to the present invention, showing the configuration thereof. With this embodiment of cartridge liquid is driven to move from a tank to another by applying mechanical pressure from a piston mechanism.

The tanks other than the waste liquid tank 6 have a piston-cylinder structure and provided with respective plungers 7a arranged above them. Air flow channel 6a is held in communication with the atmosphere. When loading the cartridge 1 in the apparatus main body (not shown), link rods 7 that are interlocked with a mechanism belonging to the apparatus main body are arranged above the respective plungers 7a. As either of the plungers 7a is pressed down by means of the corresponding link rod 7, only the liquid in the corresponding tank can be driven to move toward the waste liquid tank 6. The rate at which liquid is fed can be controlled by the moving distance of the link rod 7. Alternatively, the waste liquid tank 6 may have a piston-cylinder structure and provided with a plunger 7a arranged above it. Then, the waste liquid tank 6 can draw the liquid of some other tank as the plunger 7a is pulled away. With this alternative arrangement, each of the other tanks needs to be provided with an air flow channel and a mechanism for opening and closing the air flow channel under control and the link rod that corresponds to the single plunger needs to be provided with a hook mechanism for pulling up the plunger. Still alternatively, a mechanism for combining the pushing and the drawing actions can be used.

FIG. 4 illustrates another embodiment of cartridge according to the present invention, showing the configuration thereof. With this embodiment of cartridge, liquid is driven to move from a tank to another by means of a pinch roller mechanism. A pinch roller mechanism is devised to intermittently scrape a flexible and elastic member by means of roller showing undulations on the surface. The lateral wall of a space of the flow channel is made of an elastic material and the roller is driven to rotate, while being pressed against the lateral wall from the outside. Then, the substance that fills the space defined by the elastic member and protruding parts of the roller is driven to move in the sense of rotation of the roller. When the cartridge 1 is loaded in the apparatus main body (not shown), the pinch roller 8 is arranged relative to the diaphragm 8a of an elastic material while the blast pipes 3b, 4b are pressed against the air flow channels 3a, 4a respectively. Air blown through the blast pipes 3b, 4b is controlled only by opening and closing the respective valves for the air flow rate. The air flow channel 6a is held in communication with the atmosphere. As either of the tanks 3 and 4 is opened and the pinch roller is driven to rotate, only the liquid in the selected tank is driven to move toward the waste liquid tank 6. The rate at which liquid is fed to the waste liquid tank 6 is controlled by controlling the revolutions per unit time of the pinch roller 8.

For driving liquid in any of the above-described embodiment, the drive force is applied from the drive force transmission means arranged at the apparatus main body side and connected to the top surface of the cartridge. The part of the cartridge where the air flow channels 3a, 4a, the plunger 7b and the elastic diaphragm 8a are arranged on the top surface of the cartridge constitute the drive force input section of the cartridge for receiving drive force from the apparatus main body.

The sensor signal output section and the drive force input section are collectively arranged on the top surface of the cartridge in each of the embodiments illustrated in FIGS. 2 through 4. By arranging collectively the sensor signal output section and the drive force input section on the same surface, the cartridge is always accessed in the same direction from the apparatus main body. Particularly when a plurality of cartridges having the same structure are loaded in the apparatus main body in parallel with each other as will be described hereinafter by referring to FIGS. 6A and 6B, such an arrangement allows an easy and efficient access from the apparatus main body. Additionally, the analysis system can be downsized with ease when the sensor signal output section and the drive force input section are collectively arranged on the same surface.

From the viewpoint of downsizing, an arrangement realized by rotating the configuration described in FIG. 1 by 90° so as to laying them flat may also be permissible as a matter of option. Such an arrangement is effective when sensors are electric sensors and an enhanced degree of alignment is not required for accessing the cartridges.

For the purpose of the present invention, a ceiling surface refers to the surface that faces upward when a cartridge is loaded in the apparatus main body. In other words, a ceiling surface may not necessarily be a planar surface. A surface profile other than planar may be utilized for the purpose of the present invention. For example, a much more complex profile may be introduced to raise the strength of the cartridge and/or for the purpose of engagement with the apparatus main body. Furthermore, the profile of the ceiling surface may be optimally selected by taking the structure of the drive force input section and the positional arrangement of the components on the ceiling surface into consideration.

Although neither illustrated in the drawings nor described above, it is important to seal the one or more than one sites where the air flow channels communicate with the atmosphere. A specimen should not move by its own weight during the period from the time when the specimen is injected into the cartridge and the time when the injection port is closed. Additionally, when the cartridge contains the liquid reagent in advance, it is important that the reagent tank does not operate as an open system before use (before the cartridge is loaded in the apparatus main body). When such a site is open to the atmosphere, problems such that a liquid can leak by vibrations, that a solvent can evaporate to change the density of the reagent and that impurities can come into the scene can arise. These and other problems can be eliminated by sealing the sites where the air flow channels communicate with the atmosphere. Known sealing materials such as a laminate of resin/aluminum can be used for the purpose of sealing the communication sites. Preferably, the seals that close the communication sites are automatically destroyed when the cartridge is loaded. In the case of the embodiments illustrated in FIGS. 2 and 4, the seals are preferably broken when the blast pipes are pushed into the cartridge from the apparatus main body.

A technique for reliably protecting the reagent may be such that the part linking the reagent tank and the corresponding flow channel is provided with a diaphragm that can be destroyed by a thrust from the outside.

Liquid may be fed for the purpose of the present invention by supplying drive force from the apparatus main body side as in the case of the above-described embodiments. Alternatively, a cartridge may contain a drive element in the inside.

For example, a heat emitting element or a piezoelectric element may be arranged on part of the wall of the related flow channel. Such an arrangement may suitably be used when only a small quantity of liquid is contained in the cartridge.

Each of the blast pipes of the embodiment of FIG. 2 may be brought into communication with the inside of the cartridge by driving a fine injection needle type pipe arranged at the front end of the blast pipe to run through the flexible and elastic diaphragm (12 in FIG. 5A) such as a rubber sheet that closes the aperture of the corresponding air flow channel. With this arrangement, the cartridge is open relative to the apparatus main body when the injection needle type pipe is driven to run through the diaphragm and restores the hermetically sealed condition when the injection needle type pipe is pulled out from the diaphragm. This arrangement allows the corresponding valve at the apparatus main body side to be omitted to consequently simplify the overall configuration. Additionally, the elastic diaphragm operates as the above described seal.

Figure 5A:
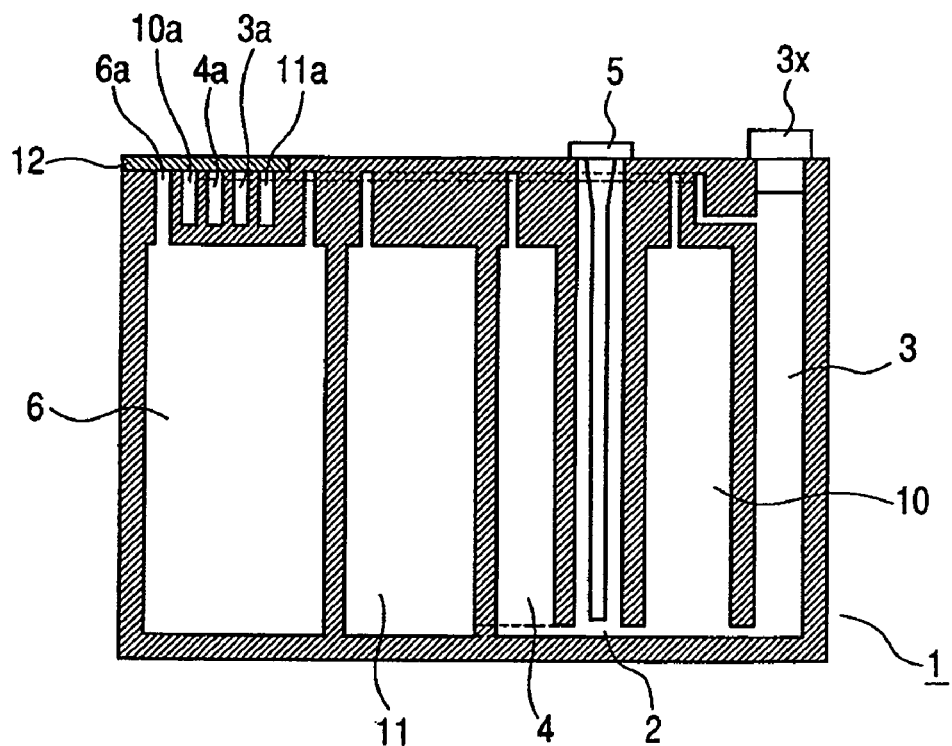
FIGS. 5A, 5B and 5C are schematic illustrations of a cartridge, showing the configuration thereof.
Figure 5B:
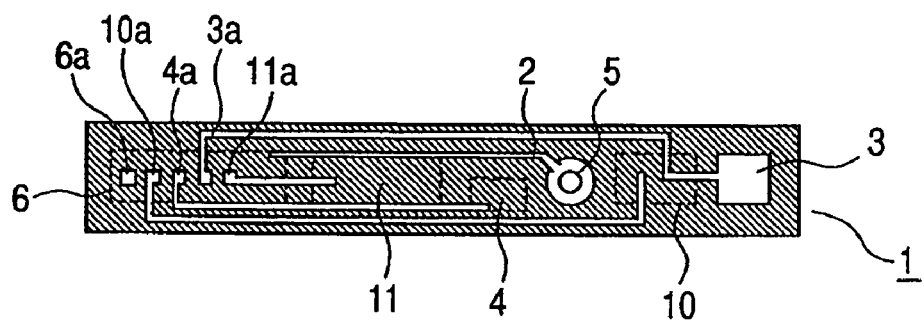

While the communication sites of the blast pipe and the like are shown right above the corresponding tanks in FIGS. 2 and 4, it is desirable to extend a plurality of air feed pipes in an upper part of the cartridge so that they may be located close to each other in a small area (see FIG. 5B). With this arrangement, the apparatus main body may be made to show a simplified configuration.

Figure 5C:
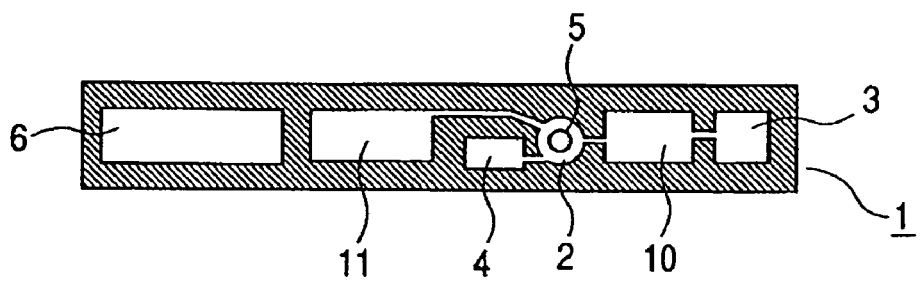

Depending on the purpose of measurement, two or more than two different types of liquid may have to be mixed with each other. For example, the specimen to be analyzed and the reagent may have to be mixed before the measurement and the specimen may have to be diluted with some liquid. Additionally, it may be desirable to add a washing step (rinsing step) after forcing the sensor to be passed through by the specimen and the reagent. Any of such requirements may be met by appropriately increasing the number of tanks in the cartridge. FIGS. 5A through 5C illustrate a cartridge designed to meet some of such requirements, showing the configuration thereof.

The cartridge of FIGS. 5A through 5C has a mixing tank 10 arranged between the specimen tank 3 and a part of the flow channel where a sensor is arranged. With this arrangement, it is possible to firstly mix the reagent contained in the mixing tank in advance with the specimen fed from the specimen tank 3 and then feed the mixed solution to the part of the flow channel where the sensor 5 is arranged. The cartridge of FIGS. 5A through 5C also has a washing liquid tank 11 so that the sensor can be washed after each step to operate more reliably and accurately for a plurality of detection processes. In other words, it is always possible to conduct a detection process on the mixed solution remaining in the mixing tank by means of the sensor 5.

For the purpose of mixing different types of liquid in the mixing tank 10, it is useful to arrange a mechanism for agitating the liquid in the mixing tank 10. A jet flow can be generated to agitate the liquid in the mixing tank by arranging a nozzle-like structure at the part linking the related liquid feeding flow channel and the mixing tank or providing the inner wall of the mixing tank with one or more than one appropriate projections. Note, however, such an agitation effect may not be reliable when the liquid in the mixing tank is highly viscous and/or contains suspended matters. A technique that can be used for more reliable agitations may be containing a magnetic agitator in the mixing tank in advance and driving it to rotate in a non-contact manner by means of a rotary magnet arranged in the apparatus main body. Other techniques that can be used for reliable agitations include arranging a vibrator element on the outer wall surface of the mixing tank or at an appropriate position of the apparatus main body where the vibrator element contacts the mixing tank or its vicinity when the cartridge is loaded in the apparatus main body so that the vibrations of the element are transmitted to the liquid in the mixing tank. Such a vibration element may be a mechanism comprising an eccentric motor or a piezoelectric element.

It is preferable to fill the waste liquid tank 6 with a material that absorbs liquid. According to the present invention, the cartridge intended to be entirely disposed with its contents after use. The waste liquid in the inside of the cartridge is effectively prevented from leaking to the outside when the waste liquid tank 6 is filled with a liquid absorbing member. Additionally, waste liquid may be fed to the waste liquid tank smoothly because the liquid absorbing member operates to draw liquid. Materials that can be used for the liquid absorbing member include known porous materials and gelling materials.

Porous materials that can be used for the purpose of the present invention include those produced by adhesively binding paper fibers and polypropylene fibers with gaps and beads of porous ceramic materials. Gelling materials that can be used for the purpose of the present invention include hydrophilic polymeric cross-linked materials such as polyacrylamide and self-organizing low molecular weight gelling agents.

Known devices comprising a solid state sensor can be used as measurement means for measuring the object of measurement, although the use of a sensor adapted to output optical or electric signals is preferable from the viewpoint of exchanges of measurement signals between the apparatus main body and the cartridge.

A measurement means that utilizes optical signal comprises a sensor that can output an optical signal representing a quantity of the object substance of measurement or a change in the quantity and a detection means that receives the optical signal from the sensor and obtains data necessary for detecting the presence or absence of the object substance of measurement and, if the presence of the object substance is detected, measuring the quantity of the object substance. The measurement means may include a data processing means for identifying the type and the quantity of the object substance of measurement on the basis of the obtained data and according to a program prepared in advance. Optical signals that can be mused for the purpose of the present invention include those that can be transmitted to the detection means arranged at the apparatus main body side according to the quantity of the object substance of measurement detected on and in the vicinity of the surface of the sensor by means of intensity of light or spatial distribution of intensity of light. Highly generally applicable optical signals that can be used for the purpose of the present invention include those that are based on optical absorption, fluorescence and emission of light. Here, optical absorption refers not only to absorption of light of one or more than one specific wavelengths by means of a so-called coloring matter or a chromophore but also to changes in (including modulations of) a physical wavelength due to plasmon resonance or the presence of nano-particles. For the purpose of the present invention, emission of light may be chemiluminsecence, phosphorescence or photostimulated emission of light but not limited thereto. Apparatus of various different types comprising a measurement means that utilizes any of such optical signals have already been proposed and an appropriate one may be selected for use for the purpose of the present invention.

Sensors that can output operation signals include light transmitting solids that can output or input and output light. The use of an optical waveguide that propagates light, causing internal total reflection to take place, is preferable for the purpose of the present invention. Not only the front end facet but also the lateral surface of an optical waveguide can be used as effective operating surface.

While there are no limitations to the profile of optical waveguide for the purpose of the present invention, profiles that can suitable be used for a cartridge according to the present invention include plate-shaped, fiber-shaped and thin-film-shaped ones. An optical waveguide having an oblong profile is preferable because it can provide an increased number of times of internal total reflection per unit volume and hence raise the efficiency of utilization of incident light.

If, for example, the object substance of measurement absorbs light of a particular wavelength, reflected light or transmitted light that is obtained by irradiating the liquid specimen with light for measurement is input to the optical waveguide that operates as sensor and then to the detection means, which may typically be a spectrometer, arranged at the apparatus main body side and connected to the optical waveguide to obtain the light absorption spectrum of the liquid. Then, it is possible to detect the presence or absence of the object substance of measurement and, if the presence of the object substance is detected, measure the quantity of the object substance. As pointed out earlier, the detection means at the apparatus main body side may be provided with a data processing means so that the obtained light absorption spectrum may be analyzed to a program prepared in advance and, if necessary, subjected to arithmetic operations in order to automatically detect the presence or absence of the object substance of measurement and, if the presence of the object substance is detected, measure the quantity of the object substance. When optical signals take the form of fluorescence, excited light is irradiated onto the liquid specimen and the obtained fluorescence is taken up to the detection means at the apparatus main body side by way of the optical waveguide to detect the presence or absence of fluorescence of a predetermined wavelength and, if the presence of such fluorescence is detected, measure the quantity thereof. In such a case again, the detection means at the apparatus main body side may be provided with a data processing means so that the obtained light absorption spectrum may be analyzed according to a program prepared in advance and, if necessary, subjected to arithmetic operations in order to automatically detect the presence or absence of the object substance of measurement and, if the presence of the object substance is detected, measure the quantity of the object substance. When plasmon resonance is utilized, a measurement means that can measure plasmon resonance is arranged in the detection means at the apparatus main body and light for obtaining plasmon resonance is irradiated onto the liquid specimen so that the presence or absence of plasmon resonance may be detected and, if the presence of plasmon resonance is detected, the intensity thereof may be measured by means of the detection means arranged at the apparatus main body side. In such a case again, the detection means at the apparatus main body side may be provided with a data processing means so that the obtained light absorption spectrum may be analyzed according to a program prepared in advance and, if necessary, subjected to arithmetic operations in order to automatically detect the presence or absence of the object substance of measurement and, if the presence of the object substance is detected, measure the quantity of the object substance.

When the liquid specimen needs to be irradiated with light in order to obtain optical signals from the sensor, necessary light may be irradiated onto the liquid specimen from the above described optical waveguide. The irradiation of light onto the liquid specimen may alternatively be conducted by means of an optical system separate from the optical waveguide and the optical system connected to the optical waveguide. However, an arrangement where the optical waveguide and the optical system connected to it can both irradiate the liquid specimen with light and take out light to be measured is preferable from the viewpoint of simplifying the configuration of and downsizing the detection system.

An appropriate one of known contact type and non-contact type connectors that are generally used for connecting optical waveguides and optical fiber cables may be selected to connect the output terminal or output/input terminal of the sensor arranged on the ceiling surface of the cartridge and adapted to output optical signals and the detection means arranged at the apparatus main body side.

Electric signals include electric currents and potential differences. Sensors adapted to output electric signals include field effect transistors, charge coupled elements and quartz oscillators in addition to electrodes that are generally used as sensors. Additionally, an arrangement where signals are taken up firstly by means of an optical means, or a light receiving element, which operates as sensor and exchange signals with the apparatus main body by way of an electric system may also be feasible for the purpose of the present inventions.

An appropriate one of known popular connectors may be selected to connect the output terminal or output/input terminal of the sensor arranged on the ceiling surface of the cartridge and adapted to output electric signals and the wiring of the detection means arranged at the apparatus main body side.

It is useful to immobilize a substance that is selectively coupled with the particular object substance of measurement contained in the liquid specimen to the surface of the sensor. Substances that can be selectively coupled with the object substance of measurement for the purpose of the present invention include antibodies, antigens, DNA (dioxyribonucleic acid), RNA (ribonucleic acid), enzymes, receptors, sugar chains and ligands (for metallic ions etc.). The present invention can find applications for analysis/measurement in various technological fields including those of medical are, foods, environment and chemicals by selecting the type of the sensor and the substance to be immobilized to the surface of the sensor.

The cartridge may be made of one or more than one materials selected from metals, resins and ceramic materials depending on the object of analysis and the internal configuration of the cartridge. For example, if a cartridge is to be used in the technological field of medical care or foods, polypropylene that is little adsorptive may be a good choice. Glass and/or silicon may be used when it is desirable to collectively manufacture the electric sensor and the entire cartridge. The use of one or more than one opaque materials is preferable when stray light can give rise to problems in a system based on optical means and when the contained reagent can be degraded by light.

Preferably, a transparent material that shows an appropriate refractive index depending on the wavelength of light to be used for measurement may selectively be used for the optical waveguide. For example, if the liquid to be handled is water, a resin material such as polystyrene or an inorganic material such as glass can be selected.

Beside signals, pieces of information such as the presence or absence of a loaded cartridge, the contents of the cartridge such as reagent and the state of feeding liquid in the cartridge may be exchanged between the cartridge and the apparatus main body. If necessary, the cartridge may be provided with one or more than one markers and/or one or more than one additional sensors for detecting such pieces of information.

Figure 6A:
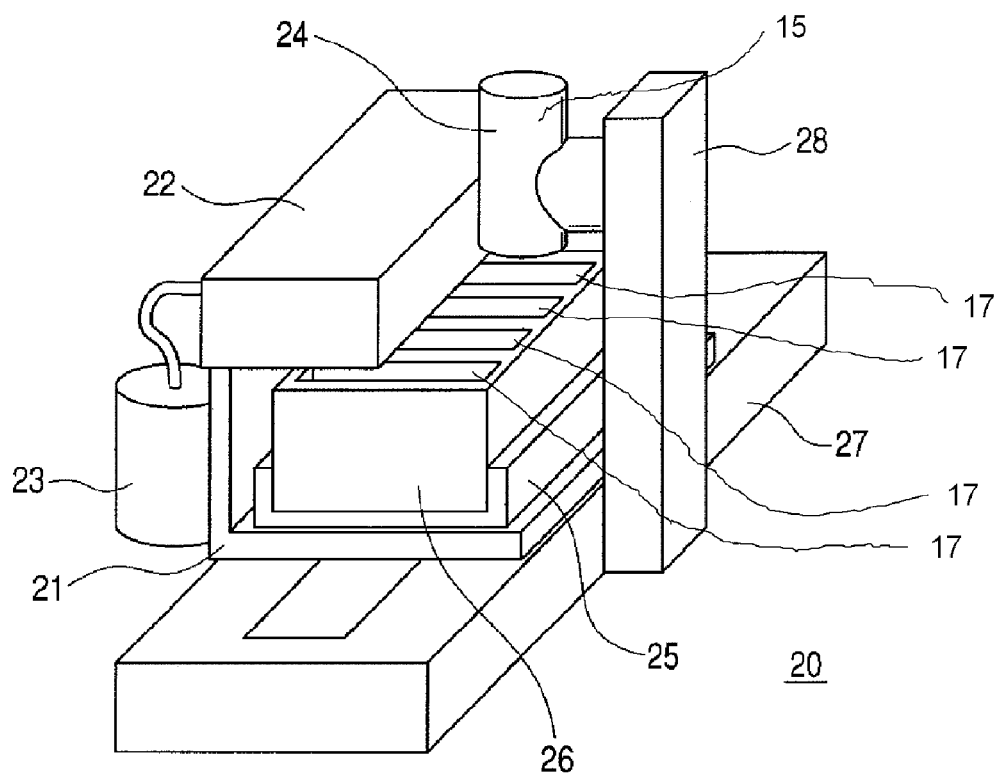
FIG. 6A is a schematic illustration of the apparatus main body of an analysis system and FIG. 6B is a schematic illustration of cartridges loaded in part of the magazine rack.
Figure 6B:
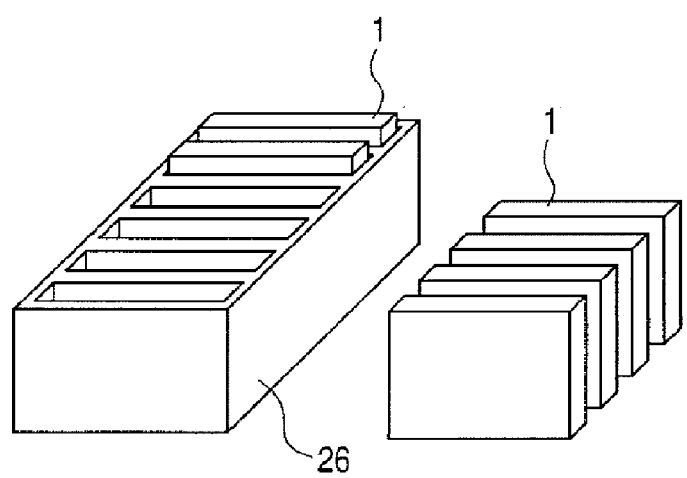

The above-described cartridge shows a rectangularly parallelepipedic profile with it longitudinal direction agreeing with the vertical direction (longitudinal direction of the drawings). However, the profile of a cartridge is not limited to rectangular parallelepiped and may alternatively be that of a thin and flat plate. In short, when a plurality of cartridges are arranged side by side in a row as shown in FIG. 1 and FIGS. 6A and 6B, it is advantageous for downsizing purpose that the lateral surfaces that are located vis-à-vis the lateral surfaces of the adjacent cartridges are oblong and rectangular and extend in the vertical direction whereas the lateral surfaces that form the lateral sides of the row of the cartridges are sufficiently narrow. In other words, it is preferable that a cartridge according to the present invention is flat and plate-shaped or rectangularly parallelepipedic and its broadest surfaces are orthogonal relative to the ceiling surface. Additionally, when a plurality of cartridges are arranged in parallel with each other, it is preferable that the ceiling surface of each of them is directed in the first direction so as to face the detecting section while the above described broadest surfaces are located vis-à-vis relative to each other.

FIGS. 6A and 6B show an example of apparatus main body. The apparatus main body comprises as principal components a horizontally movable stage 21, a valve unit 22 rigidly secured to the stage and a vertically movable optical system 24. In the valve unit 22, a pipe (not shown) led in from an air pump 23 is branched and each of the branches is linked to a vertically movable injection needle type pipe (not shown) by way of a solenoid valve. The injection needle type pipe functions just like the blast pipes 3b, 4b illustrated in FIG. 2.

A tray 25 is arranged on the stage 21 in such a way that it can be pulled out toward the foreground from the position it takes when the stage 21 comes to the extremity of the foreground side. A plurality of cartridge 1 are arranged just like those of FIG. 1 in a magazine rack 26 and the magazine rack 26 is put on the pulled out tray 25. As the tray 25 is pushed back, the tray checking sensor (not shown) arranged in the apparatus main body detects it and injection needle type pipes (not shown) are automatically lowered from the valve unit 22 and linked to (pierced into) the predetermined respective connecting sections of the cartridges 1. In the apparatus, the optical system 24 for receiving the optical signal from the optical waveguide of each of the cartridges 1 is arranged on the support pillar 28 that is rigidly secured to a substantially middle point of the range of arrangement of the cartridges 1 of the apparatus main body. The optical system 24 is vertically movable, using the support pillar 28 as guide. As the stage 21 is driven to move horizontally, a desired one of the cartridges is brought to a position right below the optical system 24. For detecting light, the optical system 24 is guided by the support pillar 28 to move vertically and connected to the cartridge placed in position. However, conversely, the stage may be held stationary and the optical system may be driven to move horizontally. A plurality of optical systems and/or detection means may be arranged for the purpose of the present invention.

The optical signal that the optical system 24 receives, from the optical waveguide (not shown) of each of the plurality of cartridges 1 is transmitted to the detection means (not shown) from the optical system and utilized to detect the object substance of detection and quantification of the detected object substance. The detection means may be integrally formed with the optical system 24 or arranged separately from it in the apparatus main body. Still alternatively, it may be arranged separately from the apparatus main body.

The magazine rack 26 may be rigidly or removably fitted to the tray. If the magazine rack 26 is removably fitted to the tray, it may conveniently be utilized as a rack for cartridges 1 at any place separated from the apparatus main body. After use, the cartridges may be taken out one by one for waste disposal. However, from the viewpoint of risk of contamination of the specimen, it is preferable to provide a mechanism for disposing cartridges as waste without directly touching them. An example of such mechanism may be one having a lever that is fitted to a lateral surface of the magazine rack so as to be operated to open the bottom of the magazine rack that has been closed hitherto and allow the cartridges contained in it to collectively leave the rack.

EXAMPLE

In this example, cartridges having a configuration as shown in FIG. 2 were applied to a sandwich fluorescence immunoassay adapted to utilize evanescent wave excitation and the PSA (prostate specific antigen) of subjects were examined. The apparatus main body was provided with a blast system (including blast pipes 3b, 4b) for feeding air to the air flow channels 3a, 4a and an optical system 5a. The blast system had two routes by way of which air supplied by an air pump is fed to the respective injection needle type pipes and were connected to the respective air flow channels 3a, 4a by way of O-rings. The waste liquid tank was constantly held open. The optical system was adapted to inject a semiconductor laser beam (650 nm) from the optical system 5a and into the optical waveguide 5 as excitation light. The optical system 5a was also adapted to detect fluorescence of 670 to 900 nm by means of a photodiode (detection means) equipped with an optical filter for separating light emitted from the end facet of the optical waveguide. The cabinet of the cartridges 1 was prepared by digging a flow channels in a block of poly(methyl methacrylate). The optical waveguide 5 was made of polystyrene and adapted to introduce excitation light and converge fluorescence coaxially.

An anti-PSA monochronal antibody was immobilized to the surface of the optical waveguide. The anti-PSA monochronal antibody (2 µm/ml) was labeled with Cy5 bisfunctional reactive dye (available from Amersham Biosciences KK) and dissolved in phosphoric acid buffer solution (pH 7.4) containing polyoxyethylene (20) sorbitanmonolaurate (0.1 mass %) to prepare a reagent (200 µl).

Four cartridges were prepared and the reagent tank of each of the cartridges was filled with the reagent. Phosphoric acid buffer solutions (100 µl each) that contain a PSA respectively to 0.01, 0.1, 1 and 10 ng/ml were injected into the specimen tanks of the respective cartridges. The volume of the flow channel in the vicinity of the optical waveguide was about 100 µl and the operation of the pump was so set as to feed 150 µl of liquid by a single pump drive operation (to be referred to as "a volume" hereinafter), taking the dead volume of the flow channel part into consideration. The sequence of observation of each cartridge is shown below.

(1) A volume of air was blown into the specimen tank and the cartridge was held in a standby state for five minutes with the optical waveguide part filled with the specimen.

(2) Two volumes of air were blown into the specimen tank and the specimen was delivered into the waste liquid tank.

(3) A volume of air was blown into the specimen tank and the cartridge was held in a standby state for five minutes with the optical waveguide part filled with the specimen.

(4) During the standby state, a laser beam was introduced into the optical waveguide and change with time of the fed back quantity of light was observed.

(5) Two volumes of air was blown into the specimen tank and the labeled antibody solution was delivered into the waste liquid tank.

Figure 7:
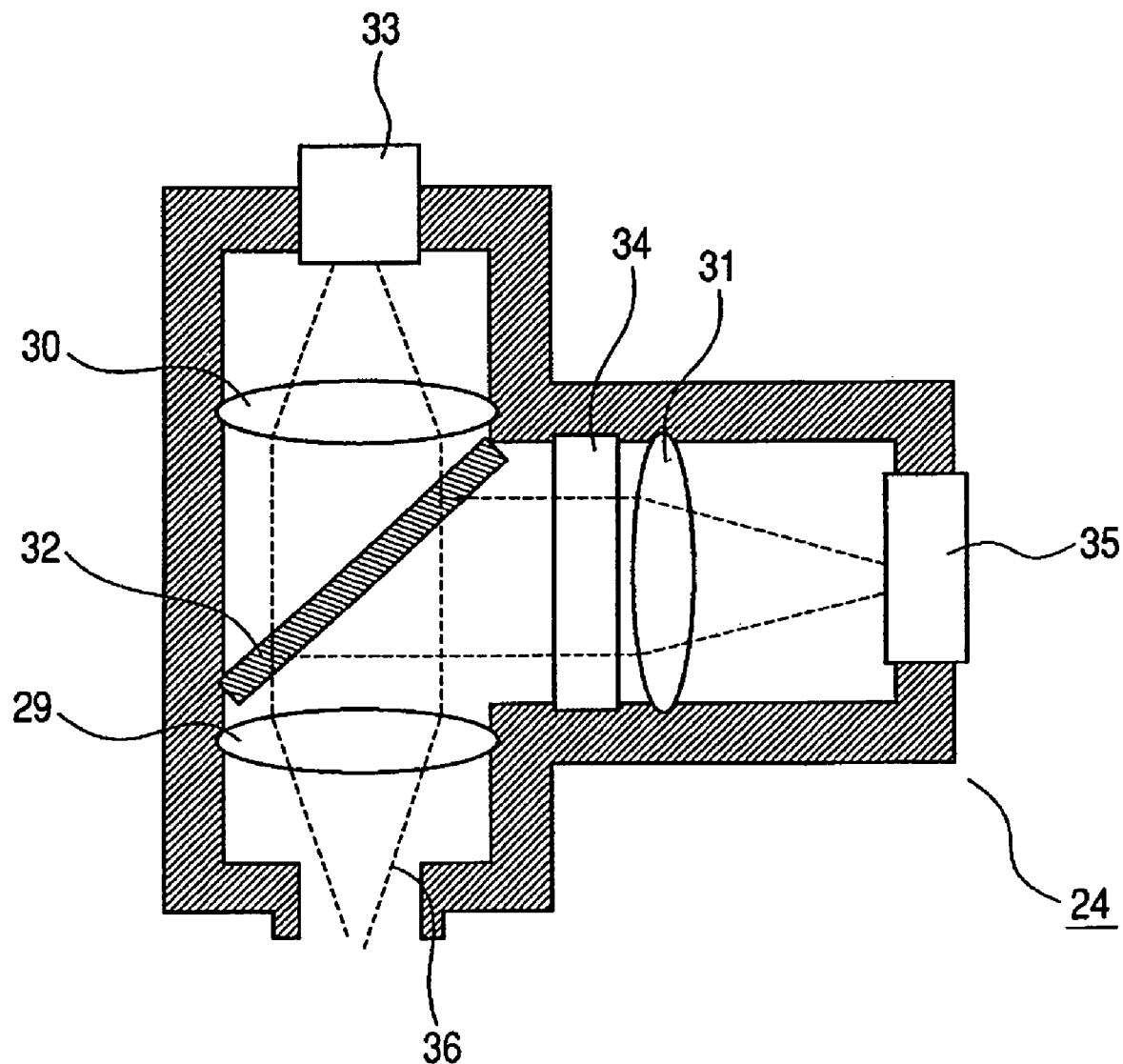
FIG. 7 is a schematic illustration of the optical system used in Example, showing the internal configuration thereof.

The increase in the quantity of light in the operation step (4) was regarded as the quantity of fluorescence from the sandwich immunocomplex at the surface of the optical waveguide. FIG. 7 is a schematic illustration of the optical unit including the optical system that was used to observe the quantity of light in the above-described example. In the optical unit, the optical system for irradiating the optical waveguide at the cartridge side from the optical channel with a laser beam coming from semiconductor laser 33 and detecting the fluorescence from the optical waveguide by means of photodiode 35 was formed by using lenses 29, 30, 31, a dichroic mirror 32 and a pigment filter 34.

The above operation was repeated four times for the specimens with different densities to obtain intensities of fluorescence signals that were proportional to the densities of the PSA.

The present invention is not limited to the above embodiments and various changes and modifications can be made within the spirit and scope of the present invention. Therefore, to apprise the public of the scope of the present invention, the following claims are made.

This application claims priority from Japanese Patent Application Nos. 2004-325393 filed on Nov. 9, 2004 and 2005-266022 filed on Sep. 13, 2005, which are hereby incorporated by reference herein.

What is claimed is:

1. A liquid analysis system designed to operate a cartridge loaded in an apparatus main body, comprising:
   an apparatus main body;
   a cartridge comprising:
      a flow channel system capable of carrying out a process on a liquid within the cartridge;
      a sensor arranged in a part of the flow channel system; and
      a ceiling surface provided with a signal output section for outputting signals from the sensor to the apparatus main body and a drive force input section for receiving a drive force for flowing the liquid from the apparatus main body,
   wherein the part of the flow channel system carrying the sensor extends in a direction allowing fluid to be fed in a vertical direction by loading the cartridge in the apparatus main body,
   wherein the cartridge has a shape having two opposite surfaces having a largest area and at least one lateral surface having a smaller area than the two opposite surfaces, one said lateral surface being the ceiling surface provided with the signal output section and the drive force input section; and
   a tray for placing a plurality of the cartridges arranged so as to face one of the opposite surfaces of each other,
   wherein the apparatus main body has:
   a reception section for receiving the signals from the signal output section, the reception section being adapted for arrangement opposite to the signal output section arranged on the ceiling surface, and
   a drive force transmission means for applying the drive force to the drive force input section, the drive force transmission means being adapted for arrangement opposite to the drive force input section arranged on the ceiling surface, and
   wherein the signal output section and the drive force input section are disposed on the ceiling surface along a straight line parallel to the two opposite surfaces having the largest area.

2. The system according to claim 1, wherein the liquid is fed through the flow channel system by increasing or reducing a pressure being applied to the liquid in the flow channel system by means of the drive force transmission means.

3. The system according to claim 2, wherein the drive force transmission means is a blast pipe and a change in pressure produced by a pump arranged in the apparatus main body is transmitted to the liquid in the cartridge by way of a gas layer.

4. The system according to claim 2, further comprising a plurality of connections by means of the drive force transmission means and sites of the connections are arranged close to each other.

5. The system according to claim 3, wherein a structure for connecting the blast pipe is such that it drives an injection needle-shaped pipe arranged at a proximal end of the blast pipe into and pulls it out from an aperture closed by a flexible and elastic diaphragm arranged in the cartridge.

6. The system according to claim 1, wherein the flow channel system includes a plurality of tanks for storing the liquid and the tanks are arranged so as to extend in the vertical direction along which the cartridge is loaded in the apparatus main body.

7. The system according to claim 1, wherein the sensor is adapted to measure at least absorption of light, fluorescence or emission of light.

8. The system according to claim 7, wherein the sensor is an optical waveguide.

9. The system according to claim 1, wherein a substance that is selectively bonded to a particular object of measurement in the liquid is immobilized to a surface of the sensor.

10. The system according to claim 9, wherein the substance is at least an antibody, an antigen, DNA, RNA, an enzyme, a receptor, a sugar chain, or a ligand.

11. The system according to claim 1, wherein the cartridge is flat and panel-shaped or rectangularly parallelepipedic and broadest surfaces thereof are orthogonal relative to the ceiling surface.

12. The system according to claim 11, wherein a plurality of cartridges are arranged so as to place their ceiling surfaces opposite to the detecting section and their broadest surfaces opposite to each other.

13. The system according to claim 1, further comprising:
   a magazine rack adapted to be removably fitted to the apparatus main body in order to load a plurality of cartridges; and
   a mechanism for moving the magazine rack horizontally in a direction of arranging the cartridges.

14. The system according to claim 13, wherein the magazine rack has a mechanism for automatically and collectively discharging used cartridges.

15. The cartridge according to claim 1, wherein the apparatus main body has a rack for holding the cartridge in such a state that the ceiling surface of the cartridge is exposed while the other surfaces of the cartridge are not exposed.

16. A cartridge for liquid analysis adapted to be loaded in an apparatus main body, the cartridge comprising:
   a flow channel system capable of carrying out a process on a liquid within the cartridge;
   a sensor arranged in a part of the flow channel system; and
   a ceiling surface provided with a signal output section for outputting signals from the sensor to the apparatus main body and a drive force input section for receiving a drive force for flowing the liquid from the apparatus main body, wherein the part of the flow channel system carrying the sensor extends in a direction allowing the fluid to be fed in a vertical direction by loading the cartridge in the apparatus main body, wherein the cartridge has a shape having two opposite surfaces having a largest area and at least one lateral surface having a smaller area than the two opposite surfaces, one said lateral surface being the ceiling surface provided with the signal output section and the drive force input section, and wherein the signal output section and the drive force input section are disposed on the ceiling surface along a straight line parallel to the two opposite surfaces having the largest area.

17. The cartridge according to claim 16, wherein the flow channel system includes a plurality of tanks for storing the liquid and the tanks are arranged so as to extend in the vertical direction along which the cartridge is loaded in the apparatus main body.

18. The cartridge according to claim 17, wherein one of the tanks is adapted to contain waste liquid after a measurement and the cartridge can be thrown out after the measurement.

19. The cartridge according to claim 17, wherein at least one of the tanks has a mechanism for agitating the liquid contained in the tank.

20. The cartridge according to claim 18, wherein a porous material or a gelling material is previously contained in the tank in a sealed state in order to prevent the waste liquid in the tank from flowing out to the outside.

21. The cartridge according to claim 16, wherein all or part of the flow channel system has a removable diaphragm or seal so as to prevent it from contacting the atmosphere before the cartridge is loaded.

22. The cartridge according to claim 16, wherein the sensor is adapted to measure at least absorption of light, fluorescence or emission of light.

23. The cartridge according to claim 22, wherein the sensor is an optical waveguide.

24. The cartridge according to claim 16, wherein a substance that is selectively bonded to a particular object of measurement is immobilized to a surface of the sensor.

25. The cartridge according to claim 24, wherein the substance is at least an antibody, an antigen, DNA, RNA, an enzyme, a receptor, a sugar chain, or a ligand.

26. The cartridge according to claim 16, wherein the liquid is fed through the flow channel system by increasing or reducing a pressure being applied to the liquid in the flow channel system.

27. The cartridge according to claim 16, further comprising a plurality of connections for receiving the drive force and sites of the connections are arranged close to each other.

* * * * *